United States Patent
Zhang et al.

(10) Patent No.: US 9,758,428 B1
(45) Date of Patent: Sep. 12, 2017

(54) ANTIMICROBIAL CHEMICALLY STRENGTHENED GLASS AND OPTIMIZATION METHOD FOR THE MANUFACTURE THEREOF

(71) Applicant: KORNERSTONE MATERIALS TECHNOLOGY COMPANY, LTD., Fuzhou, Fujian (CN)

(72) Inventors: WeiWei Zhang, Fujian (CN); Danny Cai, Fujian (CN); Frank Hung, Fujian (CN); Eric Chan, Fujian (CN); Jack Y. Ding, Fujian (CN)

(73) Assignee: KORNERSTONE MATERIALS TECHNOLOGY COMPANY, LTD., Fuzhou (CN)

( * ) Notice: Subject to any disclaimer, the term of this patent is extended or adjusted under 35 U.S.C. 154(b) by 0 days.

(21) Appl. No.: 15/494,682

(22) Filed: Apr. 24, 2017

Related U.S. Application Data (63) Continuation of application No. PCT/CN2016/080714, filed on Apr. 29, 2016.

(51) Int. Cl.
| | |
|---|---|
| *C03C 21/00* | (2006.01) |
| *C03C 3/091* | (2006.01) |
| *C03C 3/087* | (2006.01) |
| *C03C 4/18* | (2006.01) |
| *C03C 4/02* | (2006.01) |
| *A01N 59/20* | (2006.01) |
| *A01N 25/08* | (2006.01) |

(52) U.S. Cl.
CPC ............ *C03C 21/005* (2013.01); *A01N 25/08* (2013.01); *A01N 59/20* (2013.01); *C03C 3/087* (2013.01); *C03C 3/091* (2013.01); *C03C 4/02* (2013.01); *C03C 4/18* (2013.01); *C03C 2204/02* (2013.01)

(58) Field of Classification Search
None
See application file for complete search history.

(56) References Cited

U.S. PATENT DOCUMENTS

| | | | |
|---|---|---|---|
| 2012/0034435 A1 | 2/2012 | Borrelli et al. | |
| 2014/0356605 A1 | 12/2014 | Adib et al. | |
| 2015/0225288 A1* | 8/2015 | Bookbinder | C03C 21/005 428/410 |
| 2015/0239777 A1* | 8/2015 | Mauro | C03C 21/005 428/410 |
| 2017/0113967 A1* | 4/2017 | Chapman | C03C 21/005 |

FOREIGN PATENT DOCUMENTS

| | | | |
|---|---|---|---|
| CN | 105934415 | 9/2016 | |
| JP | 03146436 A * | 6/1991 | ............... C03C 3/11 |
| JP | 2011133800 | 7/2011 | |
| JP | 2014005194 | 1/2014 | |
| WO | WO 2015164556 A1 * | 10/2015 | ............. C03C 3/091 |

OTHER PUBLICATIONS

International Search Report and Written Opinion for International Application No. PCT/CN2016/080714 dated Dec. 27, 2016. (11 pages).

* cited by examiner

*Primary Examiner* — David Sample
(74) *Attorney, Agent, or Firm* — Haynes and Boone, LLP (57) ABSTRACT

An antimicrobial chemically strengthened glass and a method for manufacturing the chemically strengthened antimicrobial glass. The antimicrobial chemically strengthened glass includes an antimicrobial surface layer having at least 0.1 at % of silver ions and at least 0.1 at % of copper ions, wherein the chemically strengthened antimicrobial glass has a CIE color channel b* of less than 1.

22 Claims, 3 Drawing Sheets

ANTIMICROBIAL CHEMICALLY STRENGTHENED GLASS AND OPTIMIZATION METHOD FOR THE MANUFACTURE THEREOF

This application is a continuation of International Application No. PCT/CN2016/080714, filed Apr. 29, 2016.

FIELD OF THE INVENTION

The present invention relates to an antimicrobial chemically strengthened glass and a method for manufacturing the chemically strengthened antimicrobial glass.

BACKGROUND

As a consequence of rapid industrial growth, environmental disruption and disease have become more and more of a concern. Especially in recent years, the threat of SARS, Ebola and bird flu have raised awareness of the need for cleanliness and personal hygiene. As touch technologies proliferate, consumers are becoming increasingly aware of the possible existence of bacteria on mobile devices, particularly as touch-enabled surfaces are increasingly shared at home, work, and elsewhere. Therefore, there is an urgent need to develop effective and low cost cover glass that has antimicrobial properties.

Silver has long been known for its excellent antimicrobial properties; however, silver is relatively expensive and consequently cannot be fully utilized in industrial glass production. Most conventional antimicrobial glass has an antimicrobial layer of silver on the glass surface. Several methods are used to form this layer such as by adding silver to the raw materials for forming the glass, using silver salt spray pyrolysis, adding silver to the ion-exchange bath, coating the glass with silver, vacuum sputtering with silver and sol-gel processes for forming silver doped hybrid silicon dioxide transparent thin films from solutions that include silver nitrate and tetraethyl orthosilicate. Among such methods, adding silver to the ion-exchange bath is the most common and is the most likely technique to be used for mass production of glass having antimicrobial properties. Conventional ion exchange processes are used to chemically strengthen glass substrates and typically involve placing the glass in a molten salt containing ions having a larger ionic radius than ions present in the glass, such that the smaller ions present in the glass are replaced by larger ions from the molten salt solution. Typically, potassium ions in the molten salt replace smaller sodium ions present in the glass. The replacement of the smaller sodium ions present in the glass by larger potassium ions from the heated solution results in the formation of a compressive stress layer on both surfaces of the glass and a central tension zone sandwiched between the compressive stress layers. The tensile stress ("CT") of the central tension zone (typically expressed in megapascals (MPa)) is related to the compressive stress ("CS") of the compressive stress layer (also typically expressed in megapascals), and the depth of the compressive stress layer ("DOL") by the following equation:

$$CT = CS \times DOL/(t - 2DOL)$$

where t is the thickness of the glass.

Conventional ion exchange methods for making glass having antimicrobial properties include a one-step method in which silver is added to the conventional ion exchange bath. Glass produced by the one-step ion exchange method, however, has certain disadvantages such as silver colloidization which lowers the transmittance of visible light, low antimicrobial efficacy due to a low concentration of silver on the surface of the glass, and significant amounts of silver which reside in a deep ion exchange layer of the glass that has no effect on the antimicrobial properties of the glass.

Glass that simply incorporates silver as a component of the batch materials used to form the ion-exchangeable glass also has shortcomings. Specifically, the glass that results from such batch materials will have a low concentration of silver on the glass surface and will therefore have poor antimicrobial properties. If attempts are made to overcome this problem by including a high concentration of silver in the batch materials, the glass that results will have a visible yellow color and will have reduced antimicrobial properties due to silver colloidization caused by the high temperature ion exchange process which will lead to a decrease in the glass transmittance.

DETAILED DESCRIPTION

In several exemplary embodiments, the present invention provides chemically strengthened glass having antimicrobial properties and methods for making the chemically strengthened glass. The chemically strengthened glass has particular application as an antimicrobial cover glass for electronic displays, touch displays such as smart phones, tablets, notepads and automated teller machines, vehicle windshields and architectural structures. The chemically strengthened glass can also be used in household goods that would benefit from having antimicrobial properties such as baby bottles and glassware. As used herein the term "antimicrobial" refers to a material that has one or more of antibiotic, antibacterial, antifungal, antiparasitic and antiviral properties.

According to several exemplary embodiments, the chemically strengthened glass having antimicrobial properties is produced from an ion exchangeable glass composition that includes:

from about 50.0 to about 78.0 weight percent (wt %) of silicon dioxide ($SiO_2$), from about 1.0 to about 25.0 wt % of aluminum oxide ($Al_2O_3$), from about 0.0 to about 26.0 wt % of boron trioxide ($B_2O_3$), from about 4.0 to about 30.0 wt % of $R_2O$, wherein R=$Li^+$, $Na^+$, $K^+$; and from about 0.1 to about 18.0 wt % of R'O, wherein (R'=$Ca^{2+}$, $Mg^{2+}$, $Sr^{2+}$, $Ba^{2+}$).

According to several exemplary embodiments, the chemically strengthened antimicrobial glass has at least 0.1 at % of silver ions and at least 0.1 at % of copper ions, wherein the unit at % is atomic percentage. The chemically strengthened antimicrobial glass has a CIE color channel b* of less than 1. According to several exemplary embodiments, copper has been found to have beneficial antimicrobial properties due to its ability to exist in three valence states, namely $Cu^0$, $Cu^{1+}$ and $Cu^{2+}$. It has also been found that copper may cause a discoloration of glass, and the glass with optimized copper and silver concentrations and distributions can overcome the discoloration issue without degradation of the antimicrobial effect.

According to several exemplary embodiments, the chemically strengthened antimicrobial glass is capable of inhibiting at least 2 microbial species to an antimicrobial efficacy of greater than 99% within 24 hours. According to several exemplary embodiments, the microbial species include *Escherichia coli* and *staphylococcus aureus*.

Figure 1:
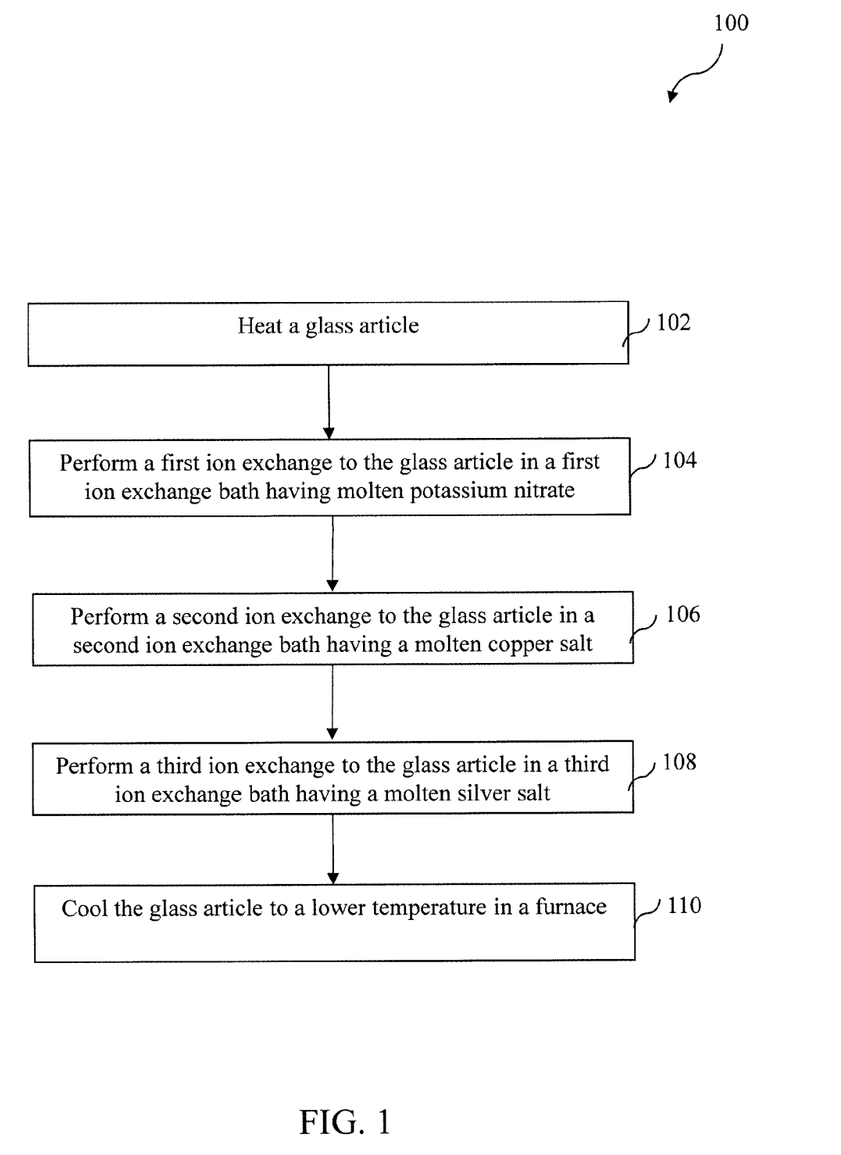
FIG. 1 illustrates a flow diagram of a method for manufacturing an antimicrobial glass article, according to certain embodiments.
Figure 2:
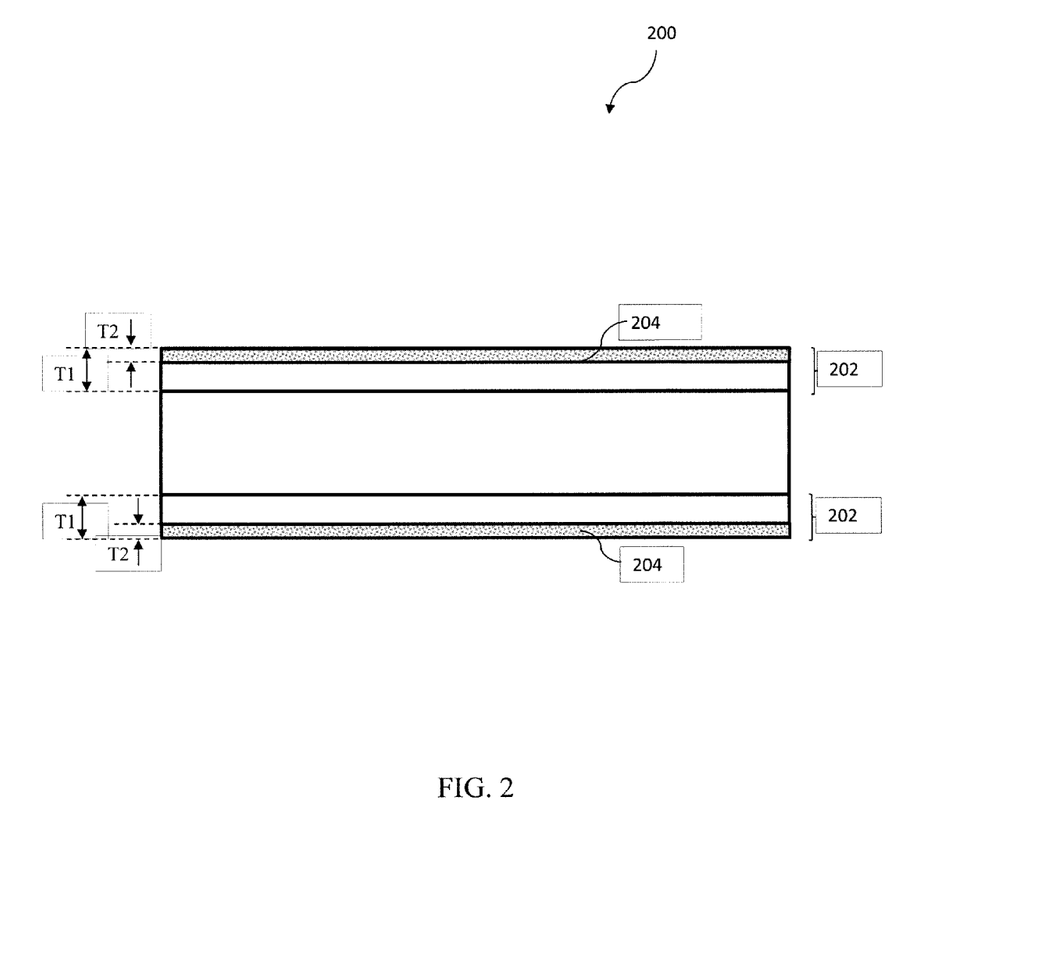
FIG. 2 illustrates a cross sectional view of an antimicrobial glass article, according to certain embodiments.

According to several exemplary embodiments, the chemically strengthened antimicrobial glass is produced by a method 100 that include a three-step ion exchange process, as illustrated in FIG. 1. A chemically strengthened antimicrobial glass 200 is illustrated in FIG. 2. The chemically strengthened antimicrobial glass 200 and the method 100 of making the same are collectively described with reference to FIGS. 1 and 2.

According to several exemplary embodiments, the glass 200 is an aluminosilicate glass that includes silicon dioxide ($SiO_2$) and aluminum oxide ($Al_2O_3$). The glass 200 further includes sodium oxide ($Na_2O$) to enable the ion exchange to generate compressive strain on the surface of the glass. In some examples, the glass 200 is an aluminosilicate glass that includes various compositions, such as from about 50.0 to about 78.0 weight percent (wt %) of silicon dioxide, from about 1.0 to about 25.0 wt % of aluminum oxide, from about 0.0 to about 26.0 wt % of boron trioxide ($B_2O_3$), from about 4.0 to about 30.0 wt % of $R_2O$, wherein R=$Li^+$, $Na^+$, $K^+$; and from about 0.1 to about 18.0 wt % of R'O, wherein (R'=$Ca^{2+}$, $Mg^{2+}$, $Sr^{2+}$, or $Ba^{2+}$). The glass 200 may be in a proper shape and size, such as a glass sheet. The glass 200 is fabricated by a suitable method, such as the overflow downdraw technique.

The method 100 includes an operation 102 to heat the glass 200 from room temperature to a temperature (such as greater than 300° C.) close to the temperature of the first ion exchange process. According to several exemplary embodiments, the glass 200 is heated to about 350° C. in about one hour.

The method 100 proceeds to an operation 104 to transfer the glass 200 to a first ion exchange bath for a first ion exchange, thereby strengthening the glass 200. During the first ion exchange process, the glass 200 is deposited in the first ion exchange bath. Relatively small ions, such as sodium ($Na^+$) are replaced by relatively large ions, such as potassium ($K^+$) at a high temperature. A strengthened layer 202 is formed on the surface of the glass 200 and substantially increases the glass mechanical strength. According to several exemplary embodiments, the first ion exchange bath includes molten potassium nitrate ($KNO_3$). In operation 104, the glass 200 is deposited in the first ion exchange bath at a first temperature (Temp1) for a first duration (D1). The first duration (D1) is greater than one hour, such as 1 hour to 8 hour. According to several exemplary embodiments, the first duration (D1) ranges between 1 hour and 1.5 hours. The first temperature (Temp1) is chosen with consideration of compressive strain and ion exchange efficiency. According to several exemplary embodiments, the first temperature (Temp1) ranges between 350° C. and 450° C. According to several exemplary embodiments, the first temperature (Temp1) ranges between 370° C. and 450° C.

The compressive stress is built in the strengthened layer 202 after it is cooled down to room temperature or other application temperature. Therefore, the strengthened layer 202 is also referred to as a compressive layer. The compressive layer 202 may be further strengthened during the subsequent ion exchanges. The compressive layer 202 includes potassium (K) introduced during the first ion exchange (and additionally introduced in the second and third ion exchanges described later). According to several exemplary embodiments, the compressive layer 202 has a thickness T1 greater than 10 microns, such as 10 microns-20 microns. The compressive layer 202 has a compressive stress greater than 500 MPa, such as at least 600 MPa, at least 800 MPa, or at least 1000 MPa, after it is cooled down.

After the first ion exchange bath, the glass 200 is removed from the first ion exchange bath. The method 100 proceeds to an operation 106 to transfer the glass 200 to a second ion exchange bath for a second ion exchange. According to several exemplary embodiments, the second ion exchange bath includes a copper compound, such as a molten copper salt. According to several exemplary embodiments, the molten copper salt includes copper chloride ($CuCl_2$), copper sulfate ($CuSO_4$), copper nitrate ($Cu(NO_3)_2$), or various combinations thereof.

The second ion exchange bath further includes molten potassium nitrate ($KNO_3$) with a substantially greater weight percentage relative to the copper salt. According to several exemplary embodiments, the second ion exchange bath includes 98~99 wt % potassium nitrate and 1~2 wt % copper salt.

In the operation 106, the glass 200 is deposited in the second ion exchange bath at a second temperature (Temp2) for a second duration (D2). The second duration (D2) is substantially shorter than the first duration (D1). According to several exemplary embodiments, the second duration (D2) is less than 30 minutes. According to several exemplary embodiments, the second duration (D2) ranges between 1 min and 30 min, between 1 min and 20 min, or between 1 min and 10 min. The second temperature (Temp2) is chosen with consideration of incorporating copper for antimicrobial effect and optical characteristics of the glass. According to several exemplary embodiments, the second temperature (Temp2) is lower than the first temperature (Temp1). According to several exemplary embodiments, the second temperature (Temp2) ranges between 350° C. and 430° C.

After the second ion exchange bath, the glass 200 is removed from the second ion exchange bath. The method 100 proceeds to an operation 108 to transfer the glass 200 to a third ion exchange bath for a third ion exchange. According to several exemplary embodiments, the third ion exchange bath includes a silver compound, such as a molten silver salt. According to several exemplary embodiments, the molten silver salt includes silver nitrate ($AgNO_3$).

The third ion exchange bath further includes molten potassium nitrate ($KNO_3$) with a substantially greater weight percentage relative to the silver salt. According to several exemplary embodiments, the third ion exchange bath includes 99.0~99.99 wt % potassium nitrate and 0.01~1.0 wt % silver salt.

In the operation 108, the glass 200 is deposited in the third ion exchange bath at a third temperature (Temp3) for a third duration (D3). The third duration (D3) is substantially shorter than the first duration (D1). According to several exemplary embodiments, the third duration (D3) is less than 30 minutes. According to several exemplary embodiments, the third duration (D3) ranges between 1 min and 30 min, between 1 min and 20 min, or between 1 min and 10 min. The third temperature (Temp3) is chosen with consideration of incorporating silver for antimicrobial effect and optical characteristics of the glass. According to several exemplary embodiments, the third temperature (Temp3) is lower than the first temperature (Temp1) and the second temperature (Temp2). According to several exemplary embodiments, the third temperature (Temp3) ranges between 350° C. and 420° C. According to several exemplary embodiments, each of the first, second, and third temperatures is tuned in a range from 350° C. to 500° C.

By the operations 106 and 108, an antimicrobial layer 204 is formed on the surface of the glass 200. The antimicrobial layer 204 includes bactericidal components, particularly, including at least 0.1 at % of silver ions and at least 0.1 at % of copper ions, wherein the unit at % is atomic percentage. According to several exemplary embodiments, the antimicrobial layer 204 includes copper ions in a range between 0.1 at % and 0.5 at % and silver ions in a range between 0.1 at % and 0.5 at %. According to several exemplary embodiments, the antimicrobial layer 204 includes at least one of $Cu^+$, $Cu^{2+}$, and $Cu^0$ introduced in the second ion exchange and $Ag^+$ introduced in the third ion exchange. Due to various factors, such as the ion exchange durations (D2) and (D3) being substantially shorter than the first ion exchange duration (D1); atomic sizes or atomic radii (the atomic radii of copper and silver are less than the atomic radius of potassium); and process design (the first ion exchange process using potassium nitrate is first implemented and the potassium is further introduced to the glass in the second and third ion exchanges), the bactericidal component is introduced to the glass in a very thin layer. According to several exemplary embodiments, the antimicrobial layer 202 has a thickness (T2) that is less than 5 μm. Accordingly, the antimicrobial layer 204 constitutes only a small portion of the compressive layer 202.

After the third ion exchange process in the operation 108, the glass 200 is removed from the third ion exchange bath and is still at a higher temperature (such as 350° C.). Still referring to FIG. 1, the method 100 proceeds to an operation 110 to cool down the glass 200 in an annealing furnace for a certain length of time, such as one hour or less. Particularly, the glass 200 is cooled down from the high temperature to room temperature or a temperature close to room temperature. According to several exemplary embodiments, the glass 200 is cooled from about 350° C. to a temperature lower than 100° C., such as about 80° C. in an hour.

According to several exemplary embodiments, the method 100 includes other operations for improving or preparing the glass 200 for various tests. According to several exemplary embodiments, the method 100 includes an operation to soak the glass 200 in water for a period of time, such as in a range from 10 minutes to 1 hour, after cooling down at the operation 110. According to several exemplary embodiments, the soaking time is greater than 20 minutes, such as about 30 minutes. According to several exemplary embodiments, the method 100 further includes an operation to clean the glass 200 with distilled water multiple times, such as more than 5 times, until the glass 200 has the desired antimicrobial effect.

As noted above, the formed glass 200 has antimicrobial effect, strengthened surface and optimized optical performances. According to several exemplary embodiments, the compressive layer 202 has a compressive stress greater than 700 MPa and has a thickness T1 greater than 5 microns.

The antimicrobial layer 204 provides high antimicrobial effect with an antibacterial activity R greater than 3. The antibacterial activity R is defined as below. When antibacterial activity R>5, it indicates 99.999% bacteria being killed; antibacterial activity R>4, indicates 99.99% bacteria being killed; and antibacterial activity R>3, indicates 99.9% bacteria being killed.

Especially, due to the concentrations and distributions of copper and silver in the antimicrobial layer 204, the glass 200 has improved optical properties. The glass 200 has a CIE color channel b* of less than 1. According to several exemplary embodiments, the CIE color channel b* of the glass is less than 0.5. The CIE color channel b* is an optical parameter defined in an L*a*b* color space by the International Commission on Illumination (CIE). The L*a*b* color space includes all perceivable colors in a three-dimensional real number space. The lightness, L*, represents the darkest black at L*=0, and the brightest white at L*=100. The color channels, a* and b*, represent true neutral gray values at a*=0 and b*=0. The red/green opponent colors are represented along the a* axis in the range from −128 to +128, with green at negative a* values and red at positive a* values. The yellow/blue opponent colors are represented along the b* axis in the range from −128 to +128, with blue at negative b* values and yellow at positive b* values. Furthermore, the glass 200 has a transmission of more than 90% in transmittance in 400~550 nm wavelength. According to several exemplary embodiments, the glass 200 has a transmission of more than 96% in transmittance in 400~550 nm wavelength.

All of the above-described characteristics of the glass 200 are achieved by the structure of the glass 200 and the method 100 making the same. This is more apparent when being compared to antimicrobial glass formed by a procedure having a two-step ion exchanges. The two-step (2-step) method introduces Ag and Cu ions to provide antimicrobial properties. The 2-step method uses a first ion-exchange bath containing $AgNO_3$, followed by ion-exchange using a second ion-exchange bath containing Cu compounds. The first silver-containing ion-exchange bath is used for a much shorter time than the second bath. In the first step, the ion exchange time is less than 1 hour at a temperature in the range of 380~500° C. In the second step, the ion exchange time is more than 1 hour at a temperature in the range of 380~500° C., so that a higher concentration of copper ions are exchanged into the surface of the glass and replace the alkali metal ions.

A first glass sample "A" was made by the method 100 having the three ion exchange steps described above. A second glass sample "B" was made by the two-step ion exchange process discussed above. In each case, the glass samples or a control blank were washed five times with distilled water before the tests.

Particularly, the glass sample "A" was a glass sheet and was prepared by the following procedure. The glass sheet was placed in a high temperature furnace. The temperature was increased from room temperature to 350° C. in 1 hour. Afterward, the glass sheet was transferred to 400° C. $KNO_3$ molten salt for chemical strengthening and was deposited therein for 3 hours. Then, the glass sheet was transferred to a molten salt that contains 1~2 wt % $CuSO_4$ and 98~99 wt % $KNO_3$ and was deposited therein for 1 min~5 min for ion exchange. Thereafter, the glass sheet is transferred in a molten salt that contains 0.01~0.2% $AgNO_3$ and 99.99%~99.8% $KNO_3$ (in weight percentage) and was deposited therein for 1 min~5 min ion exchange. Then the glass sheet was transferred to an annealing furnace to cool down from 350° C. to 80° C. in 1 hour. Thereafter, the glass sheet was soaked in water for 30 min and then was cleaned more than five times by distilled water until the glass sheet reaches its antimicrobial properties.

Figure 3:
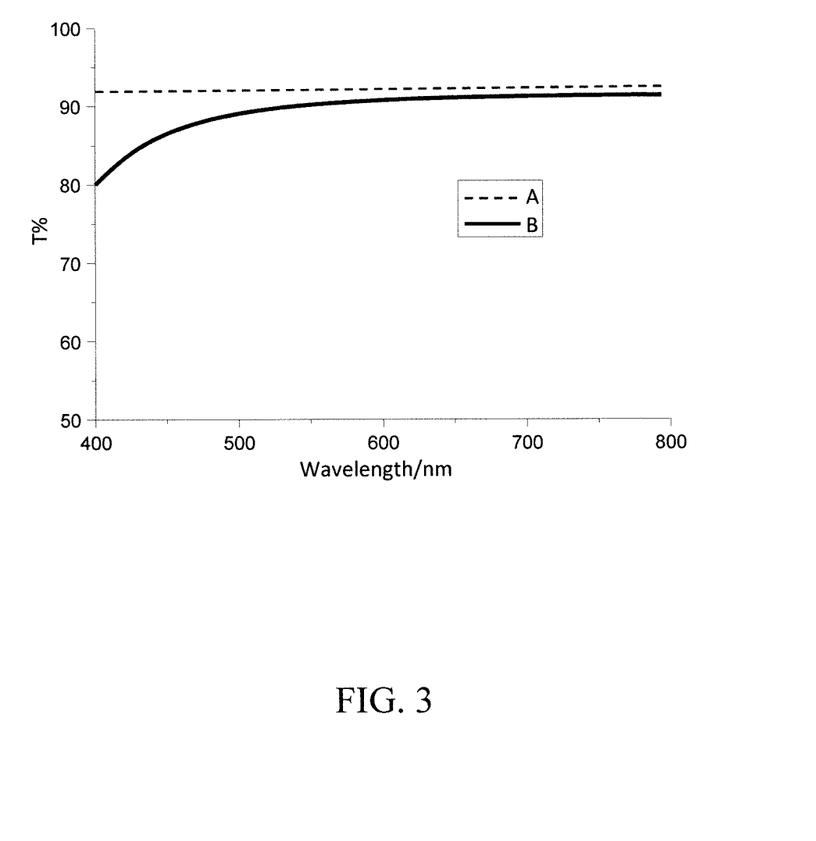
FIG. 3 illustrates diagrammatically the transmission of antimicrobial glass articles, according to certain embodiments.

The two glass samples "A" and "B" were tested for optical properties and compared below. FIG. 3 illustrates diagrammatically the optical transmissions of the two glass samples "A" and "B". In FIG. 3, the horizontal axis represents light wavelength in units of nanometers (nm) and the vertical axis represents light transmission T in percentage (%). The sample "A" has an optical transmission of more than 90% in the wavelength range of 400 nm to 800 nm, which is similar to the optical transmission of the glass before the ion exchange processes were conducted. The sample "B" has a lower optical transmission of between 80% and 90% in the wavelength range of 400~550 nm.

Table 1 below illustrates the measured CIE L*a*b* values for glass samples A and B as well as a control sample that was not ion exchanged.

TABLE 1

| Item | L* | a* | b* |
|---|---|---|---|
| Control | 96.88 | −0.09 | 0.23 |
| A | 96.83 | −0.05 | 0.27 |
| B | 96.06 | −0.95 | 3.65 |

As shown in TABLE 1, sample A had a CIE b* value of 0.27, which is very close to the CIE b* value of the control blank. Also, sample B had a CIE b* value of 3.65 and sample B appeared to be yellow to the naked eye.

The glass 200 was further analyzed by other tests and measurements for optical reliability, such as optical performance variation over various conditions. Light aging tests showed that the glass 200 appeared no difference in color and spot (i.e. no changes in appearance), after solar radiation simulation tests. According to several exemplary embodiments, the light aging test was designed as described below. The aging chamber was set to a temperature of 40° C., relative humidity (RH) of 93±3%. A xenon arc lamp was used, with a filter of daylight and radiation energy at 575 W/m$^2$ (300 nm~800 nm). The radiation procedure was set as 24$h$ for one cycle: irradiating 8 hours and turning off the lamp 16 hours. The test was repeated three times with a total duration of 72 hours. Thereafter, the changes of the antibacterial specimen were observed and measured.

Humidity and heat tests showed that the glass 200 appeared no different in color and spot after those tests, such as damp heating or thermal cycling. According to several exemplary embodiments, the humidity and heat test was designed as described below. An antibacterial test piece was placed in an aging incubator at a temperature of 40° C. and relative humidity of 93±3% for 96 hours. Thereafter, the changes that appeared in the antibacterial specimen were observed and measured.

Solvent resistance tests showed that the glass 200 appeared no different in color and spot after these tests, such as a medical alcohol resistance test. According to several exemplary embodiments, the solvent resistance test was designed as described below. A layer of medical alcohol was coated on the antibacterial test piece and the antibacterial test piece was kept in an environment of 15° C.~35° C. temperature and 45%~75% relative humidity for 24 hours. Thereafter, the changes that appeared in the antibacterial specimen were observed and measured.

In the method 100 and the glass 200, the bactericidal components (copper and silver ions) are introduced into the glass 200 through the second and third ion exchanges in substantial shorter durations (D2) and (D3) than the first duration (D1) of the first ion exchange, in which the potassium ions are introduced to the glass to form the strengthened layer 202. Accordingly, the durations (D2) and (D3) (associated with the antimicrobial layer 204) can be independently adjusted to optimize the antimicrobial layer 204 while the first duration (D1) can be adjusted to optimize the strengthened layer 202. Thus, in the 3-step ion exchange of the method 100, the thickness T1 of the antimicrobial layer 204 is controlled to be less than 5 μm. Furthermore, in the 3-step ion exchange of the method 100, the copper and silver contents in the antimicrobial layer 204 are also independently adjustable through the second and third ion exchanges, respectively. For example, the adjustable parameters for this purpose include durations (D2) and (D3) and weight percentages (of the copper in the second ion exchange bath and of the silver in the third ion exchange bath). Thus the discoloration issued is eliminated from the formed glass 200 and the formed glass 200 also has a CIE value b* of less than 1. Other fabrication factors, such as the sequence of the copper and silver ion exchanges, may also contribute to the characteristics of the glass 200.

The glass sample "A" made by the method 100 was also tested for its antimicrobial effect. Table 2 below illustrates the antimicrobial activity of the glass sample "A" and Table 3 below illustrates the antimicrobial activity of the glass sample "A" after light aging tests.

TABLE 2

| Name of test | | | The average of the common logarithm of the number of viable bacteria (cfu/cm$^2$) that recovered from the different contact time | | |
|---|---|---|---|---|---|
| bacteria (Strain number) | Concentration of bacteria (cfu/mL) | of test inoculum (mL) | / | at "0 h" contact time | at "24 h" contact time | Value of antimicrobial activity |
| Escherichia coil ATCC 8739 | 1.5 × 10$^6$ | 0.2 | Sample Control | / 4.00 | 0.24 5.70 | 5.5 |
| Staphylococcus aureus ATCC 6538P | 1.1 × 10$^6$ | 0.2 | Sample Control Sample | / 4.20 | 0.50 5.55 | 5.1 |

TABLE 3

| Name of test bacteria (Strain number) | Concentration of bacteria (cfu/mL) | | The average of the common logarithm of the number of viable bacteria(cfu/cm$^2$) that recovered from the different contact time | | Value of antimicrobial activity |
|---|---|---|---|---|---|
| | | / | at "0 h" contact time | at "24 h" contact time | |
| Escherichia coli ATCC 8739 | 1.6 × 10$^6$ | Sample | / | 0.87 | 3.2 |
| | | Control Sample | 4.30 | 4.07 | |
| Staphylococcus aureus ATCC 6538P | 1.2 × 10$^6$ | Sample | / | 0.57 | 4.5 |
| | | Control Sample | 4.22 | 5.07 | |

As shown in TABLES 2 and 3, the glass sample "A" has an antimicrobial activity R that is greater than 5 before the light aging tests (shown in the last column of TABLE 2) and greater than 3 after the light aging tests (shown in the last column of TABLE 3). The corresponding antimicrobial tests, procedures and calculations are further described below.

The antibacterial activity R value of a glass sample is calculated using the following formulae:

$$N=(C \times D \times V)/A$$

where N is the number of viable bacteria (per 1 cm$^2$ of test piece); C is the count of bacterial colonies (average count of colonies of two petri dishes adopted); D is a dilution factor; V is the volume (ml) of Soya Casein Digest Lecithin Polysorbate (SCDLP) broth used for wash-out; and A is the surface area (cm$^2$) of the covering film. When the count of bacterial colonies <1, the number of viable bacteria N is calculated by setting C=1. For example, when V is 10 ml, A is 16 cm$^2$, and D is 1, the count of colonies is represented by "<0.63".

When the test is valid, the antibacterial activity value calculated according to the formula, to retain the first decimal point while the second decimal point place is obtained by rounding. When the count of colonies "<0.63", the "0.63" is calculated as the average of logarithm number.

$$R=(U_t-U_0)-(A_t-U_0)=U_t-A_t$$

where R is antibacterial activity; $U_0$ is the average of logarithm numbers of viable cells immediately after inoculation on untreated test pieces; $U_t$ is the average of logarithm numbers of viable cells after inoculation on untreated test pieces after 24 hours; and $A_t$ is the average of logarithm numbers of viable cells after inoculation on the antibacterial test pieces after 24 hours.

The antimicrobial efficacy of the ion-exchanged glass samples produced in accordance with the glass sample "A" above was evaluated according to the following process.

Escherichia coli and staphylococcus aureus were cultivated and the cultures were transferred to nutrient agar medium and incubated for 24 hours at 37° C. The cell cultures were transferred 2 times in a row to take fresh bacteria and were then diluted ten times to a final bacterial concentration of approximately (5-10)×10$^5$ colony-forming units per milliliter (cfu/mL). Next, 0.2 mL of bacteria droplets were placed on the selected glass surface (untreated specimen (the control) or treated specimen (A)).

The cell suspension was placed onto each sample surface and held in close contact by using a sterilized laboratory parafilm (size 4 cm*4 cm, thickness 0.05 mm), and was incubated for 24 hours at 37° C., at a relative humidity (RH) ≥90%. Each sample was produced in triplicate. After 24 hours of incubation, 10 ml of SCDLP broth was added into each Petri dish. The untreated specimen, the treated specimen and the parafilm were washed. After fully shaking, 1 ml of washing solution was collected from each Petri dish and completely mixed with 9 ml sterile phosphate buffered saline. Next, ten-fold serial dilutions of the mixtures were made. Then 1 ml samples of each diluted solution were taken and placed into sterile petri dishes, such that two parallel samples per diluted solution were made. The following procedure includes adding 46~48° C. plate count agar into each petri dish; placing at room temperature environment, and flipping the petri dish after solidification. After a further 40-48 hour incubation at 37° C., the bacteria colony formation on the agar plate was examined. Bacterial colonies of count between 30~300 in each plate in each dilution were calculated. If the number of bacteria colony in 1 ml eluent was less than 30, the number of all bacteria in the plates was calculated. If none, the count was recorded as <1.

According to several exemplary embodiments, the method for manufacturing chemically strengthened antimicrobial glass includes a three-step ion exchange process for introducing potassium, copper and silver ions into the glass to provide the glass with antimicrobial properties and a strengthened surface. According to several exemplary embodiments, the three-step process utilizes a first ion-exchange bath that includes potassium nitrate ($KNO_3$), followed by a second ion-exchange bath that includes $KNO_3$ and copper compounds such as copper chloride ($CuCl_2$) and copper sulfate ($CuSO_4$), and followed by a third ion-exchange bath that includes $KNO_3$ and silver nitrate ($AgNO_3$).

According to several exemplary embodiments, the first step of the ion-exchange process is conducted in an ion-exchange bath that includes potassium nitrate for a time period of from 1 hour to 4 hours at a temperature of from 370° C. to 450° C.

According to several exemplary embodiments, the second step of the ion-exchange process is conducted in an ion-exchange bath that includes a molten copper salt for a time period of less than 10 minutes at a temperature of from 350° C. to 430° C. According to several exemplary embodiments, the second step of the ion-exchange process is conducted in an ion-exchange bath that includes from 1 wt % to 2 wt % of a molten copper salt. According to several exemplary embodiments, the second step of the ion-exchange process is conducted in an ion-exchange bath that includes one or more of molten copper sulfate, copper chloride or copper nitrate.

According to several exemplary embodiments, the third step of the ion-exchange process is conducted in an ion-exchange bath that includes a molten silver salt for a time period of less than 10 minutes at a temperature of from 350° C. to 420° C. According to several exemplary embodiments, the third step of the ion-exchange process is conducted in an ion-exchange bath that includes from 0.01 wt % to 0.2 wt % of a molten silver salt. According to several exemplary embodiments, the third step of the ion-exchange process is conducted in an ion-exchange bath that includes molten silver nitrate.

According to several exemplary embodiments, the first step of the ion-exchange process that utilizes the ion-exchange bath that includes potassium nitrate is conducted for a longer time than the second step of the ion-exchange process that utilizes the ion-exchange bath that includes a copper compound and the third step of the ion-exchange process that utilizes the ion-exchange bath that includes a silver compound.

According to several exemplary embodiments, the first step of the ion-exchange process is conducted for a time period that is longer than one hour at a first temperature in the range of from 380° C. to 500° C. According to several exemplary embodiments, the second step of the ion-exchange process is conducted for a time period that is less than 10 minutes at a second temperature that is lower than the first temperature, so that a lower concentration of copper ions are exchanged into the surface of the glass to replace the alkali metal ions in the glass. According to several exemplary embodiments, the third step of the ion-exchange process is conducted for a time period that is less than 10 minutes at a third temperature that is lower than the second temperature, so that a further lower concentration of silver ions are exchanged into the surface of the glass to replace the alkali metal ions in the glass.

According to several exemplary embodiments, the method for manufacturing chemically strengthened antimicrobial glass includes a one-step ion exchange process in which silver and copper ions are introduced at the same time to form chemically strengthened glass having antimicrobial properties and without a discoloration issue. According to several exemplary embodiments, the one-step ion exchange process utilizes an ion-exchange bath that includes silver molten salt, copper molten salt and $KNO_3$ molten salt. According to several exemplary embodiments, the one-step ion exchange method is conducted for a time period of from 1 hour to 5 hours, 1 hour to 3 hours, or 1 hour to 2 hours. According to several exemplary embodiments, the one-step ion exchange method is conducted at a temperature of from 370° C. to 450° C. According to several exemplary embodiments, the one-step ion exchange method is conducted in an ion-exchange bath that includes a mass ratio of silver ions to copper ions of from 0.005 to 1. According to several exemplary embodiments, the one-step ion exchange method is conducted in an ion-exchange bath that includes a mass ratio of silver ions to copper ions of from 0.05 to 0.8. According to several exemplary embodiments, the one-step ion exchange method is conducted in an ion-exchange bath that includes a mass ratio of silver ions to copper ions of from 0.1 to 0.5.

According to several exemplary embodiments, the method for manufacturing an antimicrobial glass includes utilizing one or a combination of spray pyrolysis of molten Ag salt and Cu salt, ion exchange in an ion-exchange bath comprising Ag salt and Cu salt, coating with Ag and Cu, vacuum sputtering coating with Ag and Cu, and sol-gel for forming an Ag and Cu doped hybrid silicon dioxide transparent film, to ensure a surface concentration of from 0.1 at % to 0.5 at % of silver ions and from 0.1 at % to 0.5% at % of copper ions.

According to several exemplary embodiments, the spray-pyrolysis method includes mixing a molten copper salt and a molten silver salt according to a certain ratio; generating a spray by a sprayer from the molten salt mixture; transferring to a high temperature furnace by a carry gas (such as argon gas); evaporating the solvent from the spray; depositing the solute to form solid particles; drying; thermally decomposing the solid particles; and sintering to forming an antimicrobial surface on the glass.

According to several exemplary embodiments, the coating method includes coating one or more liquid layers of special functional material on the surface of a glass sample, in order to provide or improve the surface functions (such as providing antimicrobial function) of the glass sample. In various examples, the liquid material for coating includes polymer liquid paste, molten polymer, or polymer melt. In various examples, the coating technique includes spin coating, dip coating, air knife coating, or roll coating.

According to several exemplary embodiments, the vacuum sputtering coating method includes, under vacuum, bombarding a target using energetic particle (such as gas positive ions having several tens of electron volts of kinetic energy), which leads to surface atoms escaping from the target; and depositing onto the surface of a glass. Vacuum sputtering coating is based on energetic ion bombardment sputtering effect of the target, and is associated with glow discharge.

According to several exemplary embodiments, the sol-gel method includes uniformly mixing raw materials containing the active ingredient in liquid phase, hydrolysis and condensation chemical reaction to form a stable transparent sol in solution. The sol is then slowly polymerized to form a gel having a three-dimensional network structure. The gel network is full of solvent without fluidity. Afterward, the gel goes through drying and sintering to form a material that may have a nano-scale structure. Particularly, the sol-gel method may include forming a solution using one or more metal compounds that contain Ag and Cu; forming sol; sol-gel transition; curing; and then a low temperature treatment to form an oxide film of nanoparticles on the glass surface.

While the present invention has been described in terms of certain embodiments, those of ordinary skill in the art will recognize that the invention can be practiced with modification within the spirit and scope of the appended claims. Any spatial references such as, for example, "upper," "lower," "above," "below," "between," "bottom," "vertical," "horizontal," "angular," "upwards," "downwards," "side-to-side," "left-to-right," "left," "right," "right-to-left," "top-to-bottom," "bottom-to-top," "top," "bottom," "bottom-up," "top-down," etc., are for the purpose of illustration only and do not limit the specific orientation or location of the structure described above.

The present disclosure has been described relative to certain embodiments. Improvements or modifications that become apparent to persons of ordinary skill in the art only after reading this disclosure are deemed within the spirit and scope of the application. It is understood that several modifications, changes and substitutions are intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. A chemically strengthened antimicrobial glass comprising an antimicrobial surface layer having at least 0.1 at % of silver ions and at least 0.1 at % of copper ions, wherein the chemically strengthened antimicrobial glass has a CIE color channel b* of less than 1.

2. The antimicrobial glass, according to claim 1, wherein the CIE color channel b* is less than 0.5.

3. The antimicrobial glass, according to claim 1, wherein the antimicrobial surface layer has a thickness of less than 5 µm.

4. The antimicrobial glass, according to claim 1, comprising a compressive surface layer having a compressive stress of greater than 500 MPa and a thickness of greater than 5 microns.

5. The antimicrobial glass, according to claim 1, wherein the antimicrobial surface layer includes at most 0.5 at % of silver ions and at most 0.5 at % of copper ions.

6. The antimicrobial glass, according to claim 1, wherein the glass has a composition comprising:
from about 50.0 to about 78.0 wt % of $SiO_2$;
from about 1.0 to about 25.0 wt % of $Al_2O_3$;
from about 0.0 to about 26.0 wt % of $B_2O_3$;
from about 4.0 to about 30.0 wt % of $R_2O$, wherein R=$Li^+$, $Na^+$, $K^+$; and
from about 0.1 to about 18.0 wt % of R'O, wherein (R'=$Ca^{2+}$, $Mg^{2+}$, $Sr^{2+}$, $Ba^{2+}$).

7. The antimicrobial glass, according to claim 1, wherein the glass has an antimicrobial activity of greater than 3.

8. The antimicrobial glass, according to claim 1, wherein a bactericidal component of the antimicrobial surface layer includes $Cu^+$, $Cu^{2+}$, $Cu^0$ and combinations thereof.

9. The antimicrobial glass, according to claim 1, wherein the antimicrobial glass has a transmission to light radiation with a wavelength in a range from 400 nm to 800 nm of greater than 90%.

10. A method of making an antimicrobial glass article comprising an antimicrobial surface layer having at least 0.1 at % of silver ions and at least 0.1 at % of copper ions, wherein the chemically strengthened antimicrobial glass has a CIE color channel b* of less than 1, comprising:
depositing an ion-exchangeable glass article in a first ion-exchange bath having molten potassium nitrate for a first duration at a first temperature;
removing the ion-exchangeable glass article from the first ion-exchange bath;
depositing the ion-exchangeable glass article in a second ion-exchange bath having a molten copper salt for a second duration at a second temperature;
removing the ion-exchangeable glass article from the second ion-exchange bath; and
depositing the ion-exchangeable glass article in a third ion-exchange bath having a molten silver salt for a third duration at a third temperature, wherein the first duration is longer than the second duration and the third duration.

11. The method of making an antimicrobial glass article according to claim 10, wherein the first duration is longer than 1 hour, the second duration is shorter than 30 minutes and the third duration is shorter than 30 minutes.

12. The method of making an antimicrobial glass article according to claim 10, wherein each of the first, second and third temperatures ranges from 350° C. to 500° C.

13. The method of making an antimicrobial glass article according to claim 10, wherein the molten copper salt includes at least one of copper chloride ($CuCl_2$), copper sulfate ($CuSO_4$), and copper nitrate ($Cu(NO_3)_2$).

14. The method of making an antimicrobial glass article according to claim 13, wherein
the second ion-exchange bath further comprises molten potassium nitrate;
the amount of molten copper salt in the second ion-exchange bath ranges from 1 wt % to 2 wt %; and
the amount of molten potassium nitrate in the second ion-exchange bath ranges from 98 wt % to 99 wt %.

15. The method of making an antimicrobial glass article according to claim 10, wherein the molten silver salt includes molten silver nitrate ($AgNO_3$).

16. The method of making an antimicrobial glass article according to claim 15, wherein
the third ion-exchange bath further comprises molten potassium nitrate;
the amount of molten silver salt in the third ion-exchange bath ranges from 0.01 wt % to 1.0 wt %; and
the amount of molten potassium nitrate in the third ion-exchange bath ranges from 99.0 wt % to 99.99 wt %.

17. The method of making an antimicrobial glass article according to claim 10, further comprising:
heating the ion-exchangeable glass article to a temperature of greater than 300° C. before the depositing of the ion-exchangeable glass article in the first ion-exchange bath; and
cooling the ion-exchangeable glass article in a furnace to a temperature of lower than 100° C. after the depositing of the ion-exchangeable glass article in the third ion-exchange bath.

18. A method of making an antimicrobial glass article comprising an antimicrobial surface layer having at least 0.1 at % of silver ions and at least 0.1 at % of copper ions, wherein the chemically strengthened antimicrobial glass has a CIE color channel b* of less than 1, comprising:
depositing a glass article in a first ion-exchange bath comprising molten potassium nitrate for a first duration at a first temperature;
depositing the glass article in a second ion-exchange bath comprising a molten copper salt for a second duration at a second temperature; and
thereafter, depositing the glass article in a third ion-exchange bath comprising a molten silver salt for a third duration at a third temperature, wherein the first duration is longer than the second duration and the third duration.

19. The method of making an antimicrobial glass article according to claim 18, wherein the first duration is longer than 1 hour, and each of the second duration and the third duration is shorter than 30 minutes.

20. The method of making an antimicrobial glass article according to claim 18, wherein the first temperature is higher than the second temperature and the second temperature is higher than the third temperature.

21. The method of making an antimicrobial glass article according to claim 18, wherein
the molten copper salt comprises at least one of copper chloride ($CuCl_2$), copper sulfate ($CuSO_4$), and copper nitrate ($Cu(NO_3)_2$);
the second ion-exchange bath further comprises molten potassium nitrate;
the amount of molten copper salt in the second ion-exchange ranges from 1 wt % to 2 wt %; and
the amount of molten potassium nitrate in the second ion-exchange bath ranges from 98 wt % to 99 wt %.

22. The method of making an antimicrobial glass article according to claim 18, wherein the molten silver salt comprises molten silver nitrate (AgNO$_3$);

the third ion-exchange bath further comprises molten potassium nitrate;

the amount of molten copper salt in the third ion-exchange bath ranges from 0.01 wt % to 1.0 wt %; and the amount of molten potassium nitrate in the third ion-exchange bath ranges from 99.0 wt % to 99.99 wt %.

\* \* \* \* \*